(12) United States Patent
Krajcovic et al.

(10) Patent No.: US 7,932,385 B2
(45) Date of Patent: Apr. 26, 2011

(54) PALIPERIDONE KETONE

(75) Inventors: Jozef Krajcovic, Brno (CZ); Jiri Bartl, Strelice (CZ); Petr Benovsky, Brno (CZ)

(73) Assignee: Synthon BV, Nijmegen (NL)

( * ) Notice: Subject to any disclaimer, the term of this patent is extended or adjusted under 35 U.S.C. 154(b) by 25 days.

(21) Appl. No.: 12/501,218

(22) Filed: Jul. 10, 2009

(65) Prior Publication Data

US 2010/0069633 A1    Mar. 18, 2010

Related U.S. Application Data

(60) Provisional application No. 61/080,088, filed on Jul. 11, 2008.

(51) Int. Cl.
*C07D 239/70* (2006.01)
*C07D 239/72* (2006.01)

(52) U.S. Cl. ........................ 544/282; 544/287

(58) Field of Classification Search ............. 544/282, 544/287
See application file for complete search history.

(56) References Cited

U.S. PATENT DOCUMENTS

| | | | |
|---|---|---|---|
| 5,158,952 | A | 10/1992 | Janssen et al. |
| 5,688,799 | A | 11/1997 | Vandenberk et al. |
| 2009/0036470 | A1 | 2/2009 | Bartl et al. |
| 2009/0156810 | A1 | 6/2009 | Bartl et al. |

FOREIGN PATENT DOCUMENTS

| | | |
|---|---|---|
| EP | 0 196 132 B1 | 8/1992 |
| EP | 0 368 388 B1 | 5/1995 |
| WO | WO 95/14691 | 6/1995 |
| WO | WO 2007/026377 | 3/2007 |
| WO | WO 2008/021342 * | 2/2008 |

OTHER PUBLICATIONS

A. Horvath et al., "Nitrogen Bridgehead Compounds. Part 30. Vilsmeier-Haack Formylation of 6, 7, 8, 9 Tetrahydro-4H-pyrido [1,2-a] pyrimidin-4-ones" (J. Chem. Soc. Perkin Trans. 1, (1983) pp. 369-377.

* cited by examiner

*Primary Examiner* — James O Wilson
*Assistant Examiner* — Erich A Leeser
(74) *Attorney, Agent, or Firm* — Muncy, Geissler, Olds & Lowe, PLLC

(57) ABSTRACT

A compound of formula (7.2) or an acid addition salt thereof.

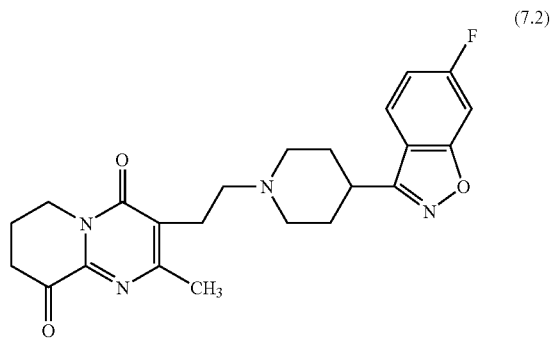

The compound can be used as a reference standard for monitoring the presence thereof in a paliperidone sample, including monitoring the completion of a paliperidone reaction. Reduction in the amount of the compound in paliperidone can be achieved by crystallization in the presence of a hydride reductant.

15 Claims, No Drawings

PALIPERIDONE KETONE

This application claims the benefit of priority under 35 U.S.C. §119(e) from U.S. Provisional application Ser. No. 61/080,088, filed Jul. 11, 2008; the entire contents of which are incorporated herein by reference.

BACKGROUND OF THE INVENTION

Paliperidone, or 9-hydroxyrisperidone (chemically: (±)-3-(2-(4-(6-fluoro-1,2-benzisoxazol-3-yl)-1-piperidinyl)ethyl)-6,7,8,9-tetrahydro-9-hydroxy-2-methyl-4H-pyrido[1,2-a]pyrimidin-4-one) of the formula (I):

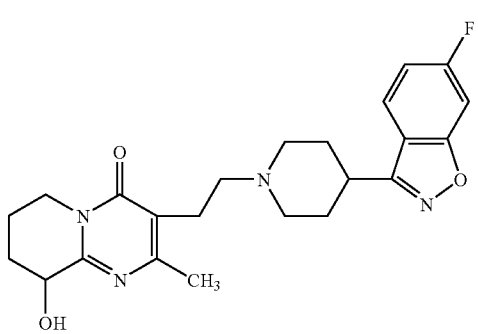

is a major human metabolite of the known antipsychotic drug risperidone and is itself an antipsychotic. It is marketed in tablets for oral administration under the brand name INVEGA™ (Janssen, L. P.) for treatment of schizophrenia. Paliperidone has one centre of optical activity (the carbon in the 9-position); both enantiomers are known but the marketed compound is a racemate.

Paliperidone (including enantiomeric forms thereof) has been disclosed in EP 368388 (U.S. Pat. No. 5,158,952). The same document discloses also esters of paliperidone with carboxylic acids having the formula (II) ($R'=C_{1-19}$ alkyl)

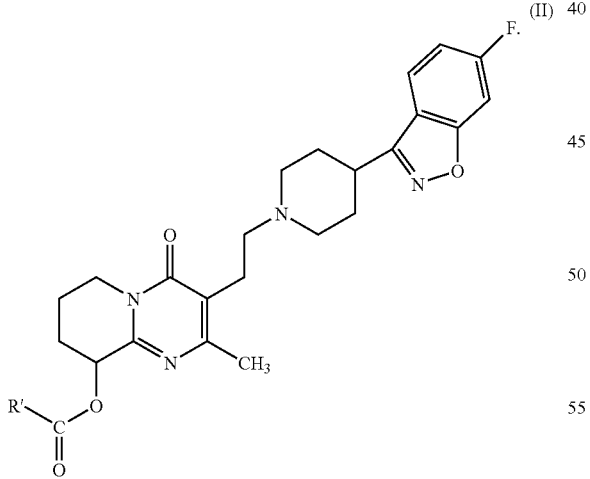

A preferred ester compound (II) is paliperidone palmitate, which is currently under development for use in injectable compositions with prolonged action.

Various processes for making compounds of formula (I) and (II) have been generally disclosed in the EP 368388 and in later documents. One process is based on an alkylation of a 3-piperidinyl 1,2-benzisoxazole of the formula (2) with the compound of formula (1.1), wherein R is hydrogen or C1-C20 acyl group and A represents an appropriate leaving group such as, for example, halo, e.g., chloro, bromo or iodo; sulfonyloxy, e.g., methanesulfonyloxy, trifluoromethanesulfonyloxy, benzenesulfonyloxy, 4-methylbenzenesulfonyloxy and the like leaving groups:

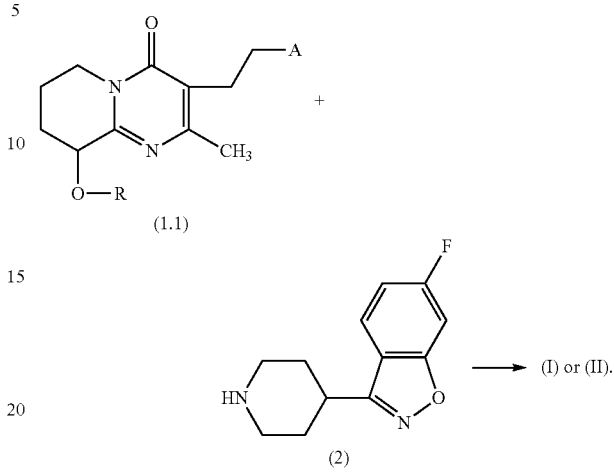

Another known process is based on the reaction of the same compound (1.1) with an oxime compound (3), wherein L is a reactive leaving group, followed by the ring closure of the isoxazole ring on the intermediate (4):

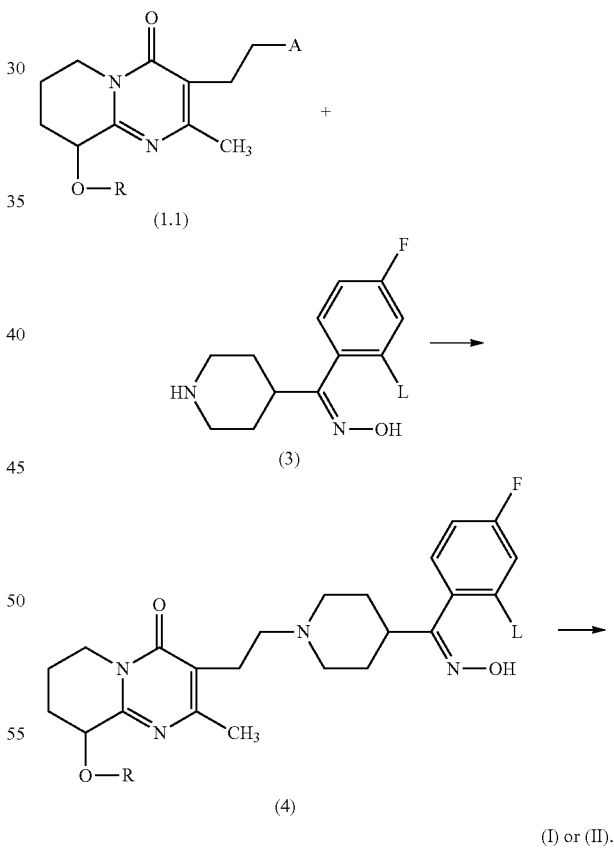

Furthermore, the esters of formula (II) may be prepared by acylating paliperidone (I) by an acylation agent (e.g. acyl halide or acyl anhydride).

The compounds of the general formula (1.1) are valuable intermediates in making paliperidone (I) as well as the paliperidone esters of the formula (II). A typical example of the intermediate of the general formula (1.1) is the compound 3-(2-chloroethyl)-6,7,8,9-tetrahydro-9-hydroxy-2-methyl-4H-pyrido[1,2-a]pyrimidin-4-one of the formula (1a)

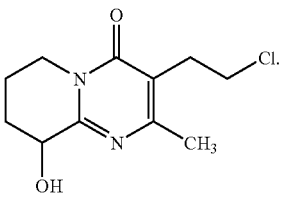

(1a)

The precise reaction mechanisms including unintended side-reactions, have not, however, been fully elucidated for the above-mentioned reaction schemes. It would be desirable to improve the control, yield, and/or purity of a process for making paliperidone or its esters.

SUMMARY OF THE INVENTION

Applicants have discovered that the synthesis of paliperidone according to the above prior art schemes, as well as the transformation thereof into pharmaceutical dosage forms (e.g. tablets or solutions), suffers from a disadvantage in that a certain amount of a keto-compound of formula (7.2) is formed as a side product.

(7.2)

To improve the manufacturing and control processes related to paliperidone, it is desirable to have the compound (7.2) prepared in an isolated state with a sufficient and defined purity, e.g., for use as a reference material during the analytical control of the synthetic and/or purification process as well as in the analytical control of the purity of the paliperidone product and its various pharmaceutical dosage forms.

Accordingly, a first aspect of the present invention is directed to a compound of formula (7.2) or an acid addition salt thereof (7.2)

in an isolated state having a purity of greater than 50%, such as greater than 80%, preferably greater than 95%.

A second aspect of the present invention is directed to a process, which comprises crystallizing crude paliperidone in the presence of a hydride reductant to form paliperidone essentially free from a compound of formula (7.2). Preferably, the hydride reductant is sodium borohydride. Typically, the hydride reductant is present in an amount of 0.01 to 0.5 molar equivalents based on the molar amount of the crude paliperidone.

A third aspect of the present invention relates to a process, which comprises assaying a paliperidone sample for the presence of a compound of formula (7.2). The paliperidone sample can be taken from a crude reaction mixture or from a presumed pharmaceutical grade paliperidone lot, e.g., received API. Taking the paliperidone sample during the synthetic reaction allows for controlling the reaction based on the result of the assaying; e.g., terminating the reaction if the amount of the compound of formula (7.2) in the paliperidone sample is below a predetermined threshold value. Alternatively, taking the paliperidone sample from a presumed pharmaceutical-grade lot or batch or paliperidone allows for quality testing and/or reprocessing of API. In one embodiment, the assaying results from the sample lead to:

a) accepting the presumed pharmaceutical-grade paliperidone lot as pharmaceutical grade if the amount of the compound of formula (7.2) in the paliperidone sample is below a predetermined threshold value; or b) rejecting the presumed pharmaceutical-grade paliperidone lot as pharmaceutical grade if the amount of the compound of formula (7.2) in the paliperidone sample is at or above a predetermined threshold value.

The rejected lot can then be subjected to crystallization in the presence of a hydride reductant to remove/reduce the compound of formula (7.2) and form a new presumed pharmaceutical-grade paliperidone lot.

The present invention also relates to the use of the compound of formula (7.2) in its isolated state as a reference material for monitoring and/or improving the course of a process for making paliperidone and/or for purification of reaction mixtures or raw materials comprising paliperidone.

DETAILED DESCRIPTION OF THE INVENTION

The present invention relates to the discovery of an isolated, including solid state form, of the compound of formula (7.2) and to various uses thereof in the synthesis of paliperidone and its acyl derivatives of the general formula (1).

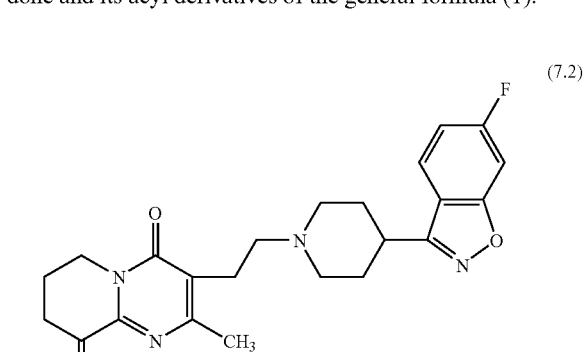

(7.2)

The formula (7.2) as used herein also embraces acid addition salts thereof.

Many processes of making paliperidone and its pharmaceutical dosage forms, as well as the storage of paliperidone in its isolated state and the pharmaceutical dosage forms, suffer from the disadvantage of forming an impurity, which was discovered and identified by the present inventors as a compound of the formula (7.2). Without wishing to be bound by theory, it is thought that this compound may be formed by aerial oxidation of the paliperidone or may be formed as a side product upon hydrolysis of an enamine (5).

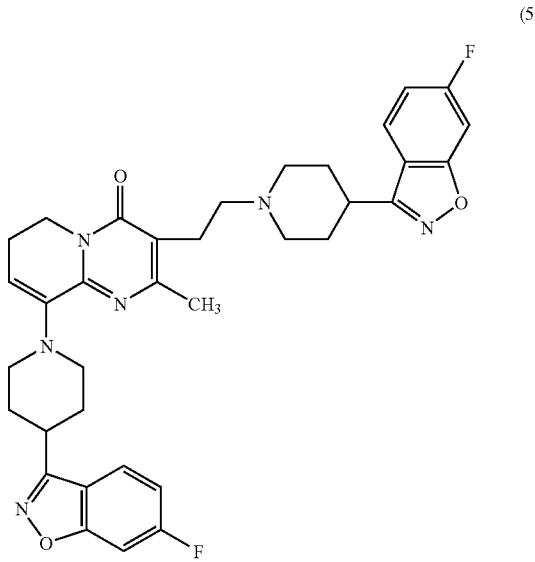

(5)

The enamine (5) may result from the condensation of an excess of the compound (2) or (3) with the reactive hydroxyl-group in the compound (1.1). The hydrolysis of the enamine (5) into (7.2) could occur during subsequent reaction steps.

Regardless of how it is formed, the presence of the compound of the formula (7.2) as a side-product in the paliperidone synthesis is undesirable. Being able to detect the compound of formula (7.2), control reaction conditions to minimize its content and/or to convert it to paliperidone is thus desirable.

Compound (7.2) in an "isolated state" refers to any product comprising the compound (7.2) having a purity greater than 50%, such as greater than 80%, and preferably greater than 90% of the compound (7.2). The "purity" of compound (7.2) relates to the presence or absence of residual solvents and reagents as well as structurally related impurities. For example, a compound (7.2) in an isolated state having a purity of greater than 85% may comprise less than 5% of residual solvents and reagents from its synthesis and less than 10% of structurally related impurities.

It was discovered that the compound of the formula (7.2) in an isolated state may be prepared by oxidation of paliperidone by a suitable oxidant, e.g., by a commercially available Dess-Martin periodinate of the below formula.

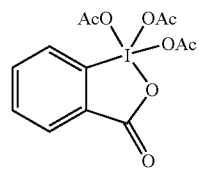

With this Dess-Martin periodinate oxidation agent, the reaction proceeds in a corresponding suitable inert solvent, such as in a hydrocarbon or a halogenated hydrocarbon solvent, and at essentially ambient temperature.

Another useful oxidation agent is sodium hypochlorite (NaClO), and a corresponding suitable inert solvent is preferably a polar aprotic solvent, e.g., acetonitrile or dimethyl formamide.

Still other useful oxidation agents include chromium trioxide and chromium (VI) salts, pyridinium chlorochromate, dimethyl sulfoxide (including in combination with dicyclohexylcarbodiimide, phosphorus pentoxide, oxalyl chloride, or trifluoroacetanhydride), manganese dioxide, silver carbonate, and acetone with potassium/aluminium alkoxide, etc.

The product (7.2) may be isolated by conventional means, e.g., by evaporation of the solvent, and further purified, e.g., by a recrystallization from a suitable crystallization solvent.

In another process, the isolated form of the compound (7.2) may also be prepared by condensation of a compound of the formula (7)

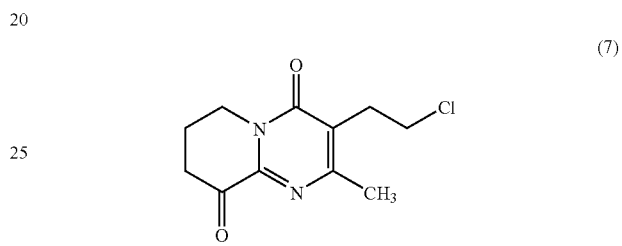

(7)

with the compound (2) or (3) similarly as indicated above for the compound (1.1). The starting compound of the formula (7) may be prepared from the compound (1.1), preferably from the compound (1a), by a reaction with a suitable oxidant, e.g., by Dess-Martin periodinate, under essentially same conditions as indicated above.

In yet another process, the isolated form of the compound (7.2) may be prepared by a reaction of an aldehyde of the formula (8)

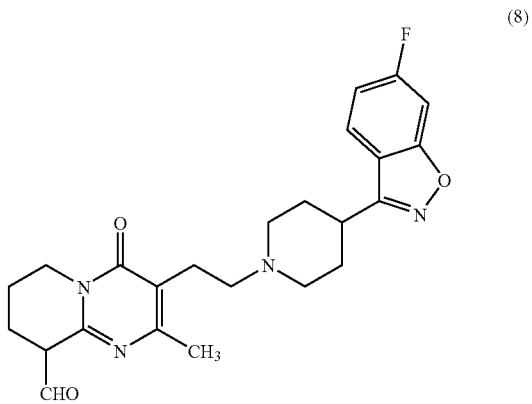

(8)

with peracetic acid. The aldehyde (8) may be obtained by a process disclosed in U.S. provisional application Ser. No. 60/952,376, filed Jul. 27, 2007, the entire contents of which are incorporated herein by reference.

The isolation of the compound (7.2) from a reaction mixture provides the compound (7.2) in a stable and handleable form with a defined quality, allowing various practical uses thereof.

For example, the isolated form of the compound (7.2) may serve as a reference standard in an analytic method for monitoring a chemical process yielding paliperidone or for monitoring stability characteristics of the obtained paliperidone product. A suitable analytical method is HPLC, though other conventional analytical techniques such as TLC can also be used. The use as a reference standard contemplates the preparation of a reference sample of the compound (7.2) in sufficient purity that the qualitative and quantitative characteristics thereof (e.g., in HPLC, retention time and a peak area of a defined amount of the reference material) can be determined. These characteristics can then facilitate the identification and/or quantification of the compound (7.2) in a sample. Thus the isolated form of the compound (7.2) facilitates assaying for its presence in various samples of paliperidone. A "paliperidone sample" is a sample taken from any substance or material that contains paliperidone; for example samples taken from a crude reaction mixture wherein paliperidone is being or has been synthesized, a solid pharmaceutical-grade paliperidone, a pharmaceutical dosage form (tablet, etc.) that contains paliperidone as an active ingredient, etc. By assaying the paliperidone sample, the relative or absolute amount of the compound (7.2) in the tested sample is determined and, accordingly, corresponding adjustment in the production, purification or storage can be made.

One example of the use of assaying relates to the synthesis of paliperidone. A paliperidone sample can be taken from a crude reaction mixture at the end of the reaction to determine the level of the compound (7.2) impurity as a quality control determination and/or to determine if further processing should be undertaken to reduce the amount of the compound (7.2). Likewise, a sample can be taken during the reaction and the result of the assay used to assist in controlling the reaction. The term "controlling" generally means adjusting the duration of the reaction, although "controlling" could also mean adjusting the temperature, pressure, amount of reducing agent, etc. In a simple example, the reaction is terminated once the amount of compound (7.2) is below a predetermined level; e.g. less than 5% more typically less than 2%, as determined by the assaying step. The reaction can be monitored such as by HPLC in order to determine when the predetermined threshold has been met.

Essentially any paliperidone synthetic process can be subject to the assaying. In a preferred embodiment, the reaction involves a conversion of risperidone to paliperidone via a reductive deoximation of an oxime as more fully described in U.S. provisional application Ser. No. 61/080,072, filed Jul. 11, 2008, the entire contents of which are incorporated herein by reference. In this co-pending application, a process according to the scheme below may be monitored for the presence of the intermediate compound (7.2) and terminated after the content of the compound (7.2) in the reaction mixture drops under a predetermined threshold, e.g., below 2%.

Another example of the use of the assaying step relates to the stability and/or purity of paliperidone in solid form, isolated form, or in solution. Based on the assaying result, the storage conditions may be adjusted or revised in such a way that the content of the compound (7.2) in the paliperidone product does not exceed a predetermined threshold.

In a particular embodiment, a paliperidone sample is taken from a presumed pharmaceutical-grade paliperidone lot and assayed for the presence of the compound of formula (7.2). The term "pharmaceutical-grade" means that the lot or batch of paliperidone has a purity of at least 98%, preferably greater than 99%. The term "presumed" refers to a lot that is thought to be pharmaceutical-grade, e.g., after an API (active pharmaceutical ingredient) manufacturer makes such a lot, after such a lot is stored, after such a lot is shipped, or after a third party received such a lot and desires to confirm the purity thereof, etc. Based on the assay of the sample, the lot can be accepted or rejected as being pharmaceutical-grade, at least with respect to the compound of (7.2). Thus, a lot would be accepted as pharmaceutical grade if the sample has an amount of the compound (7.2) below a predetermined threshold, e.g. less than 1% and more typically less than 0.5% and even less than 0.2%. Alternatively, a lot would be rejected as pharmaceutical-grade if the amount of the compound (7.2) is above a predetermined threshold. It should be noted that a pharmaceutical-grade lot would likely have additional purity requirements and thus the acceptance of the lot based on this assay would not necessarily be, nor is it required to be, the only criterion for acceptance. A rejected lot can be reprocessed to reduce the impurities to form a new presumed pharmaceutical-grade paliperidone lot, if desired, and subjected to the assaying process again.

Likewise dosage forms containing paliperidone can also be assayed and monitored for the presence of the compound (7.2). As the compound (7.2) may be a product of aerial oxidation, the process of making dosage forms of paliperidone (tablet, etc.) as well as storing these forms prior to actual use may cause the formation of the compound of formula (7.2). Accordingly, samples of paliperidone dosage forms may be assayed to monitor the presence of the compound (7.2) with the goal to adjust the process and/or storage conditions to minimize the formation of the compound (7.2) or to simply judge the quality and continued acceptability of the dosage form after a certain shelf-life.

An additional use of the compound (7.2) of the present invention is its conversion into paliperidone. The ability to convert the compound (7.2) via a reductant into paliperidone can be used to aid in the purification and/or isolation of paliperidone. In one process, the impure paliperidone is crystallized from a crystallization medium comprising a solvent and a hydride reductant, advantageously sodium borohydride. The molar amounts of the reductant may typically vary from 0.01 to 0.5 equivalents; its actual amount may be adjusted in respect to the actually present compound (7.2) in the crude paliperidone. The small amounts of the compound (7.2) present in the impure paliperidone material are converted within the crystallization process into paliperidone, so that the purity of the obtained product is significantly enhanced. In certain embodiments, the content of the compound (7.2) in a paliperidone sample after this kind of a purification process could be below the limit of detection by HPLC. Thus, after one or more such crystallization processes, the resulting paliperidone is essentially free from the compound (7.2), i.e., contains less than 5%, such as less than 3% or 2%, preferably less than 1%, and more preferably less than 0.2% of the compound (7.2). The crystallization is a convenient way to reprocess a rejected lot of paliperidone and thus create a new presumed pharmaceutical-grade lot of paliperidone as described above in connection with the assaying processes. Depending on the crystallization conditions, the solid paliperidone may be obtained in various crystalline forms, e.g., in forms disclosed in the patent application WO2008/021342.

The invention will be further described with reference to the following non-limiting examples.

EXAMPLES

Example 1

Process for Making the Keto-compound (7.2)

5.0 g of paliperidone was dissolved in 17.0 ml of dichloromethane. 5.38 g of Dess-Martin periodinane (DMP) and 0.63 ml of sulfuric acid (96%) were added into the reaction mixture and it was stirred at 0° C. for 30 minutes and at room temperature (25° C.) for 4 hours. Next amount of 1.28 g of Dess-Martin periodinane was added at T=4 h 15 min. After 6 hours the homogenous reaction mixture was diluted with 100 ml of dichloromethane and poured into 200 ml of saturated aqueous $NaHCO_3$ solution containing 10 g of sodium thiosulfate ($Na_2S_2O_3$). The mixture was stirred for 20 min. The dichloromethane layer was washed with 150 ml of saturated aqueous $NaHCO_3$ solution, 2×150 ml of water, 150 ml of brine, dried ($MgSO_4$), filtered and evaporated on rotavap. The yield of dark yellow crude product: is 2.57 g (51.6%).

The crude product was redissolved in hot acetonitrile, solid product obtained after cooling was filtered out and discarded, and the solvent was evaporated. The evaporation residue was triturated twice with hot acetonitrile to obtain a product with HPLC purity (IN) 87.7%.

Example 2

Process for Making of Keto Compound (7.2)

4.2 g of paliperidone was stirred with 50 ml of AcOH and 12.6 ml of $CH_3CN$ was added at RT. The mixture becomes clear. The solution was cooled to 0° C. and 8.4 ml of solution NaOCl (content active chlorine 140-150 g/1000 ml) was dropwise added in 1 min. The internal temperature was increased to 6° C. After 17 min the cooling bath was removed and internal temperature increased to 22° C. After 90 min reaction mixture was poured into 700 ml of brine at 0° C. The solids were filtered by suction, dissolved in acetone and solvent was evaporated (200-20 mbar, 40° C.). Solid material was obtained (slight brown color) with HPLC purity (IN) 62% with yield 76%.

Example 3

Process for Making the Keto-compound (7.2)

4.0 g of compound (8) was added portionwise into 40 ml of water and 5.1 ml of peracetic acid during 10 min at 35° C. The internal temperature increased from 35° C. to 40° C. The solid material was dissolved immediately. Into the reaction mixture, 50 ml of dichloromethane was added after 10 additional minutes. The mixture was neutralized by 20% solution of $NaHCO_3$ to pH-7.3. The layers were separated and organic layer washed with 2×40 ml of water, dried by solid sodium sulphate and filtered with activated charcoal over celite. The solvent was evaporated (30 mbar, 40° C.). The yield of white foamy material is 2 g (52%), purity 64% (HPLC IN).

Example 4

Purification Process for Removing the (7.2) from Paliperidone 40 g paliperidone (purity 98.6%, content of the impurity (7.2) is 0.35%) was dissolved in a mixture of 260 ml of water, 260 ml of isopropanol and 6.76 g of $CH_3COOH$ (1.2 equivalents) at 50° C. in a nitrogen atmosphere. The mixture was cooled to 30° C. and 11.5 ml of 2.025M aqueous $NH_3$ (0,25 equivalents) and 40 ml of the borohydride solution (0.106 g of $NaBH_4$ +20 ml of water +20 ml of isopropanol +one drop of 10% NaOH) was added. The mixture was stirred for 30 minutes at 30° C. Then, 44.5 ml of 2.025M aqueous $NH_3$ (0.95 equivalents) was added. The suspension was stirred for 1 hour. The crystals were filtered off and washed with 2×80 ml of mixture (water:isoPrOH=1:1). Yield: 33.39 g (83.5% of the theoretical yield) of the crystallized paliperidone having an HPLC purity of 99.7% and no detectable amount of (7.2).

Each of the patents, published patent applications, and provisional applications mentioned above are incorporated herein by reference. The invention having been thus described it will be obvious that the same may be varied in many ways and all such modifications are contemplated as being within the scope of the invention as defined by the following claims.

We claim:

1. A compound of formula (7.2) or an acid addition salt thereof

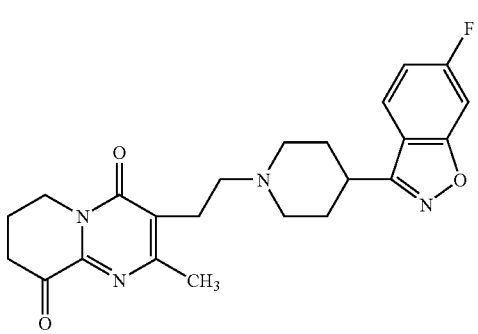

in an isolated state having a purity of greater than 50%.

2. The compound according to claim 1, wherein said isolated compound has a purity of greater than 80%.

3. The compound according to claim 2, wherein said isolated compound has a purity greater than 95%.

4. A process, which comprises crystallizing crude paliperidone in the presence of a hydride reductant to form paliperidone essentially free from a compound of formula (7.2)

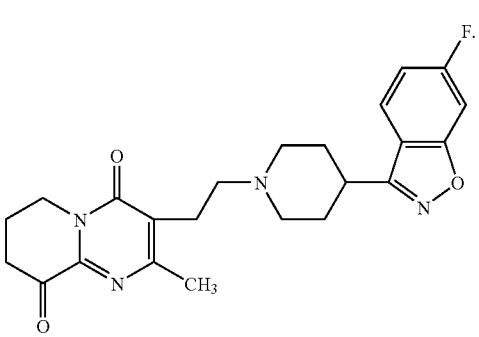

5. The process according to claim 4, wherein said hydride reductant is sodium borohydride.

6. The process according to claim 4, wherein the hydride reductant is present in an amount of 0.01 to 0.5 molar equivalents based on the molar amount of the crude paliperidone.

7. A process, which comprises assaying a paliperidone sample for the presence of a compound of formula (7.2).

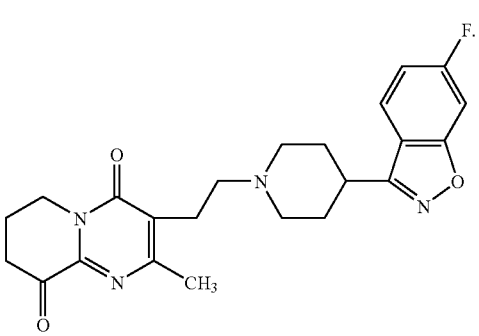

8. The process according to claim 7, wherein said paliperidone sample was taken from a crude reaction mixture.

9. The process according to claim 8, wherein said paliperidone sample was taken during said reaction and said process further comprises controlling said reaction based on the result of the assaying.

10. The process according to claim 9, wherein said controlling comprises terminating said reaction if the amount of said compound of formula (7.2) in said paliperidone sample is below a predetermined threshold value.

11. The process according to claim 7, wherein said paliperidone sample was taken from a presumed pharmaceutical-grade paliperidone lot.

12. The process according to claim 11, which further comprises:

a) accepting said presumed pharmaceutical-grade paliperidone lot as pharmaceutical grade if the amount of the compound of formula (7.2) in the paliperidone sample is below a predetermined threshold value; and b) rejecting said presumed pharmaceutical-grade paliperidone lot as pharmaceutical grade if the amount of the compound of formula (7.2) in the paliperidone sample is at or above a predetermined threshold value.

13. The process according to claim 12, wherein said rejected lot is subjected to crystallization in the presence of a hydride reductant to form a new presumed pharmaceutical-grade paliperidone lot.

14. A process of making the compound of formula (7.2.) of claim 1, which comprises oxidizing paliperidone with an oxidation agent to form said compound of formula (7.2).

15. A process for making the compound of formula (7.2) of claim 1, which comprises reacting an aldehyde of formula (8)

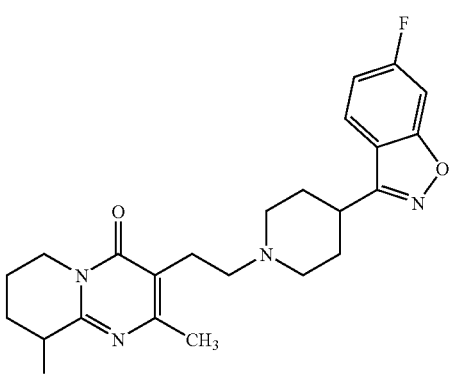

with peracetic acid to form said compound of formula (7.2).

* * * * *